(12) United States Patent
Ranucci et al.

(10) Patent No.: US 9,364,235 B2
(45) Date of Patent: Jun. 14, 2016

(54) POWER ASSIST DEVICE FOR A SURGICAL INSTRUMENT

(71) Applicant: C.R. Bard, Inc., Murray Hill, NJ (US)

(72) Inventors: Kevin J. Ranucci, Warwick, RI (US); Nathan Stewart Cauldwell, Mansfield, MA (US); Augustus Felix, Cranston, RI (US)

(73) Assignee: C.R. Bard, Inc., Murray Hill, NJ (US)

( * ) Notice: Subject to any disclaimer, the term of this patent is extended or adjusted under 35 U.S.C. 154(b) by 232 days.

(21) Appl. No.: 13/804,043

(22) Filed: Mar. 14, 2013

(65) Prior Publication Data

US 2014/0276963 A1    Sep. 18, 2014

(51) Int. Cl.
| | | |
|---|---|---|
| A61B 17/10 | (2006.01) | |
| A61B 17/068 | (2006.01) | |
| A61B 17/064 | (2006.01) | |
| A61B 17/29 | (2006.01) | |
| A61B 19/00 | (2006.01) | |

(52) U.S. Cl.
CPC .............. A61B 17/10 (2013.01); A61B 17/068 (2013.01); A61B 2017/0647 (2013.01); A61B 2017/2912 (2013.01); A61B 2017/2919 (2013.01); A61B 2017/2929 (2013.01); A61B 2019/4836 (2013.01)

(58) Field of Classification Search
CPC ........ A61B 17/10; A61B 17/068; B25C 5/06; B25C 5/10
USPC .................. 606/139, 142, 143, 151; 227/147, 227/175.1–182.1; 81/463, 464
See application file for complete search history.

(56) References Cited

U.S. PATENT DOCUMENTS

| | | |
|---|---|---|
| 2,786,450 A | 3/1957 | Jacobus et al. |
| 4,699,154 A | 10/1987 | Lindgren |
| 5,258,010 A | 11/1993 | Green et al. |
| 5,282,476 A | 2/1994 | Terwilliger |
| 5,368,045 A | 11/1994 | Clement et al. |
| 5,398,861 A | 3/1995 | Green |
| 5,458,608 A | 10/1995 | Wortrich |
| 5,601,473 A | 2/1997 | Strain et al. |
| 5,782,397 A | 7/1998 | Koukline |
| 5,921,456 A * | 7/1999 | Kirsch et al. .................. 227/147 |
| 5,997,552 A | 12/1999 | Person et al. |
| 6,010,513 A | 1/2000 | Törmälä et al. |
| 6,030,402 A | 2/2000 | Thompson et al. |
| 6,053,388 A | 4/2000 | Pfister et al. |
| 6,228,098 B1 | 5/2001 | Kayan et al. |
| 6,330,964 B1 | 12/2001 | Kayan et al. |

(Continued)

FOREIGN PATENT DOCUMENTS

| | | |
|---|---|---|
| EP | 2430985 | 3/2012 |
| WO | WO 2009/036290 | 3/2009 |

*Primary Examiner* — Thomas McEvoy
(74) *Attorney, Agent, or Firm* — Wolf, Greenfield & Sacks, P.C.

(57) ABSTRACT

A surgical instrument including a power assist device, and its method of use for deploying surgical fasteners, is disclosed. The surgical instrument may include a handle, an elongated shaft extending from the handle, and a surgical fastener deployment system including a driveshaft. The driveshaft is actuatable between at least a first proximal position and a second distal position. A striker is movable relative to the driveshaft and an impact surface is associated with the driveshaft. The impact surface is constructed and arranged to be struck by the striker member to displace the driveshaft to the second distal position and deploy the surgical fastener.

26 Claims, 7 Drawing Sheets

(56) References Cited

U.S. PATENT DOCUMENTS

| | | |
|---|---|---|
| 6,425,900 B1 | 7/2002 | Knodel et al. |
| 6,447,524 B1 | 9/2002 | Knodel et al. |
| 6,447,527 B1 | 9/2002 | Thompson et al. |
| 6,450,391 B1 | 9/2002 | Kayan et al. |
| 6,457,625 B1 | 10/2002 | Törmälä et al. |
| 6,551,333 B2 | 4/2003 | Kuhns et al. |
| 6,652,538 B2 | 11/2003 | Kayan et al. |
| 6,773,438 B1 | 8/2004 | Knodel et al. |
| 6,905,057 B2 | 6/2005 | Swayze et al. |
| 6,986,775 B2 | 1/2006 | Morales et al. |
| 7,083,075 B2 | 8/2006 | Swayze et al. |
| 7,143,926 B2 | 12/2006 | Shelton et al. |
| 7,229,452 B2 | 6/2007 | Kayan |
| 7,303,108 B2 | 12/2007 | Shelton |
| 7,481,347 B2 | 1/2009 | Roy |
| 7,485,124 B2 | 2/2009 | Kuhns et al. |
| 7,543,728 B2 | 6/2009 | Spasov et al. |
| 7,641,094 B2 | 1/2010 | Kayan et al. |
| 7,694,863 B2 | 4/2010 | Spasov et al. |
| 7,740,159 B2 | 6/2010 | Shelton et al. |
| 7,758,637 B2 | 7/2010 | Starksen et al. |
| 7,883,538 B2 | 2/2011 | To et al. |
| 7,905,893 B2 | 3/2011 | Kuhns et al. |
| 8,091,755 B2 | 1/2012 | Kayan et al. |
| 2006/0122633 A1 | 6/2006 | To et al. |
| 2008/0177307 A1 | 7/2008 | Moskowitz et al. |
| 2009/0108049 A1 | 4/2009 | Roy |
| 2010/0147919 A1 | 6/2010 | Schiestl |
| 2010/0286679 A1 | 11/2010 | Hoey et al. |
| 2010/0292710 A1 | 11/2010 | Daniel et al. |
| 2010/0292715 A1 | 11/2010 | Nering et al. |
| 2010/0312257 A1 | 12/2010 | Aranyi |
| 2011/0079627 A1 | 4/2011 | Cardinale et al. |
| 2011/0275891 A1 | 11/2011 | Shemi |
| 2012/0022557 A1 | 1/2012 | Cabiri et al. |
| 2012/0029538 A1 | 2/2012 | Reeser |
| 2012/0085807 A1 | 4/2012 | Kayan et al. |
| 2012/0283739 A1 | 11/2012 | Ralph et al. |

* cited by examiner

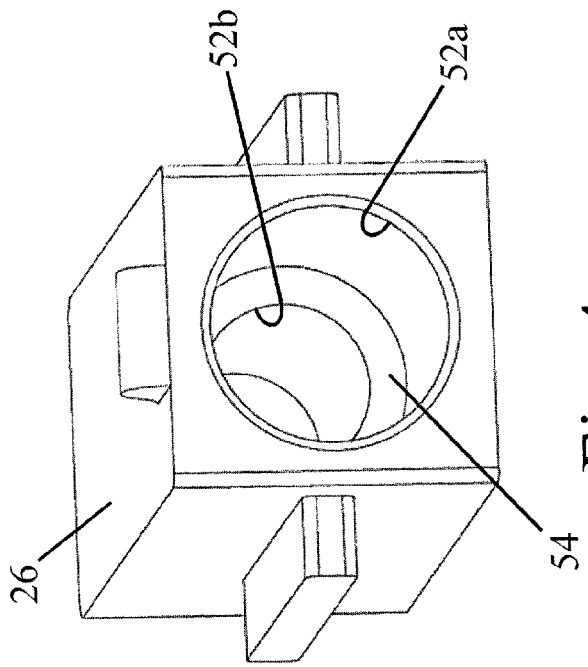
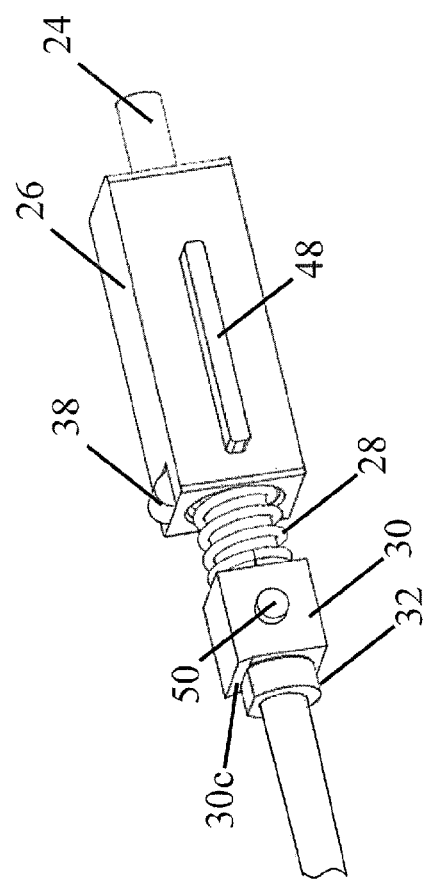
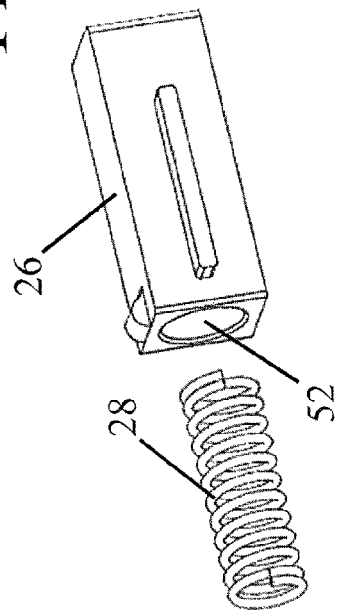
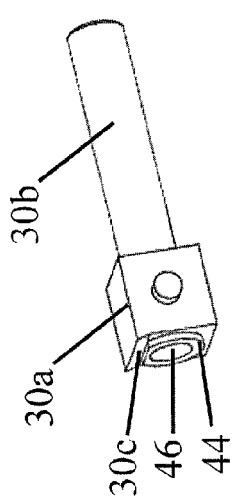
Fig. 2
Fig. 3
Fig. 4

POWER ASSIST DEVICE FOR A SURGICAL INSTRUMENT

FIELD

A power assist device for a surgical instrument.

BACKGROUND

Oftentimes a surgical mesh fabric or other prosthetic repair fabric is used during a surgical repair of a hernia. The prosthetic repair fabric may be placed in an open procedure or laparoscopically. To secure the repair fabric in place, one or more fasteners may be deployed through the prosthetic repair fabric and into the underlying tissue. The amount of force required to fire the fasteners is a function of both the fastener geometry and the type of prosthetic repair fabric used. Larger fasteners and tighter fabrics generally result in increased forces to deploy the fasteners through the prosthetic and into the underlying tissue. To reduce the necessary amount of force supplied by an operator to deploy a fastener, a laparoscopic fixation device may incorporate a power assist device to aid in deploying the fastener.

SUMMARY

In one embodiment, a surgical instrument may include a handle, an elongated shaft extending from the handle, and a surgical fastener deployment system including a driveshaft. The driveshaft is actuatable between at least a first proximal position and a second distal position. A striker is movable relative to the driveshaft. An impact surface is associated with the driveshaft and is constructed and arranged to be struck by the striker member to displace the driveshaft to the second distal position and deploy the surgical fastener.

In another embodiment, a method for deploying a surgical fastener includes: providing an instrument including a surgical fastener and a system for deploying the surgical fastener from the instrument, the deployment system including a driveshaft; displacing the driveshaft from a first position towards a second position operatively associated with deploying the surgical fastener; and applying an impulse to the displacing driveshaft to accelerate movement of the driveshaft to the second position.

In yet another embodiment, a method for deploying a surgical fastener includes: providing an instrument including a surgical fastener and a system for deploying a surgical fastener from the instrument, the deployment system including a driveshaft and an impact surface associated with the driveshaft; striking the impact surface with a moving mass; and transferring momentum from the mass to the drive shaft to deploy a surgical fastener.

It should be appreciated that the foregoing concepts, and additional concepts discussed below, may be arranged in any suitable combination, as the present disclosure is not limited in this respect.

The foregoing and other aspects, embodiments, and features of the present teachings can be more fully understood from the following description in conjunction with the accompanying drawings.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 2 is a perspective view of a power assist device mounted on a driveshaft;

FIG. 3 is an exploded view of a power assist device;

FIG. 4 is a perspective view of an energy storage member housing;

DETAILED DESCRIPTION

Figure 1:
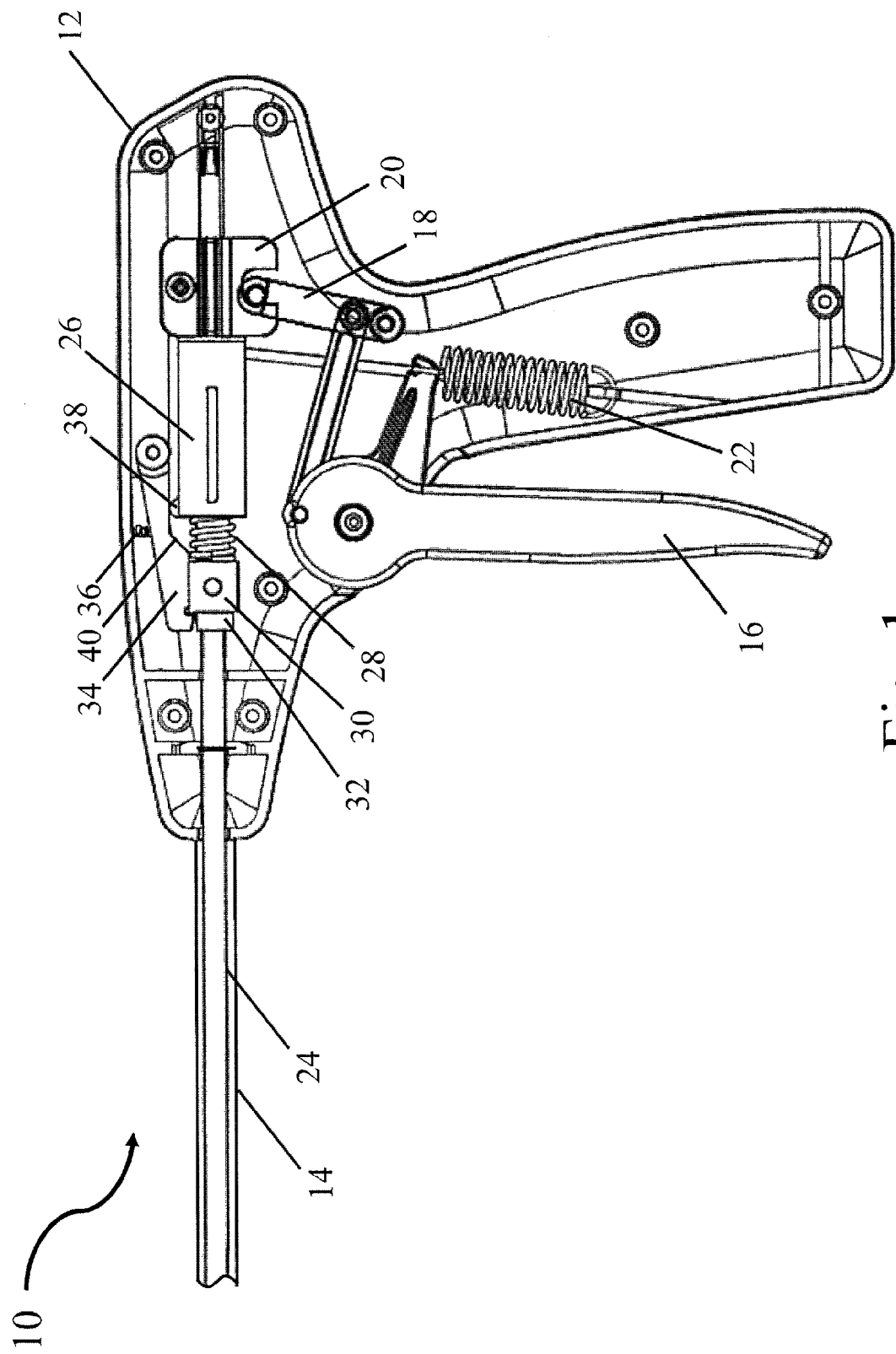
FIG. 1 is a cross-sectional view of a surgical instrument incorporating a power assist device.

The inventors have recognized the benefits associated with providing a short duration impulse to a driveshaft involved in deploying a surgical fastener from a surgical instrument. Without wishing to be bound by theory, a short duration impulse results in a larger force being applied to the fastener which may improve prosthetic fabric penetration and reduce the required manual force input from a user. The short duration impulse may also provide enhanced tactile and audible feedback for a user indicating that a surgical fastener has been deployed.

A short duration impulse may be applied to a driveshaft by striking the driveshaft with a moving mass. The driveshaft may be moving, or at rest, prior to being struck by the moving mass. The moving mass may strike the driveshaft either directly, or indirectly, to transfer momentum from the mass to the driveshaft to deploy the surgical fastener. Depending upon the particular embodiment, the driveshaft may be completely, or only partially, actuated in response to being struck by the moving mass. In instances where the driveshaft is completely actuated by the moving mass, the driveshaft may be located in a first proximal position prior to being struck and in a second distal position to deploy a fastener after being struck by the moving mass. Alternatively, in embodiments where the driveshaft is partially actuated prior to being struck, the driveshaft may be actuated from the first proximal position towards the second distal position prior to being struck by the moving mass at a predetermined position between the first proximal position and the second distal position.

In certain embodiments, the moving mass is coupled to the driveshaft. Without wishing to be bound by theory, in such an embodiment, acceleration of the mass may result in acceleration of the driveshaft in the opposite, i.e. proximal, direction. It is preferable to prevent this backwards acceleration since it would at least partially cancel out the impulse provided by the mass impacting the driveshaft. Therefore, it is desirable to substantially prevent backwards movement of the driveshaft in embodiments where the mass is coupled to the driveshaft. Preventing backwards acceleration of the driveshaft may be accomplished in any number of ways including, but not limited to, the actuation force provided by the actuation system, a ratchet mechanism, friction, or any other appropriate mechanism or physical effect capable of substantially preventing backwards acceleration of the driveshaft while still permitting the driveshaft to move in both proximal and distal directions in order to deploy one or more fasteners.

The various embodiments of the power assist device disclosed herein are not limited to any particular type of fastener or surgical instrument. For example, a power assist device could be used with a tack, clip, staple, pin, tissue anchor, bone anchor, and any other type of fastener that could benefit from the use of a power assist device to reduce the required manual force for insertion or deployment of a fastener. Similarly, the power assist device may be used to assist in any number of medical procedures including, but not limited to, attaching a fabric to underlying tissue, attaching adjacent layers of tissue, attaching identification devices and/or tags to livestock, and other appropriate applications involving the deployment of a fastener.

For the sake of clarity, the currently disclosed embodiments are directed to a laparoscopic device. However, the current disclosure is not limited to laparoscopic devices. Instead, the power assist device could be used in any appropriate device for deployment of a fastener into tissue. For example, a power assist device could be incorporated into an endoscopic device, a borescopic device, a catheter, a surgical instrument for use in "open" procedures, or any other appropriate surgical instrument. Additionally, the instrument including the power assist device may be loaded with one or more fasteners, or may be constructed to allow the user to load the instrument with one or more fasteners.

Turning now to the figures, specific embodiments of a power assist device incorporated into a surgical instrument are described.

FIG. 1 depicts a surgical instrument 10 including a handle 12 and a hollow elongated shaft 14 extending from the handle 12 towards a distal end of the device from which fasteners are deployed. The surgical instrument includes a trigger 16 which is coupled to a transmission the linkage 18. When the trigger 16 is actuated, a transmission linkage 18 displaces a shuttle 20 towards a distal end of the surgical instrument 10. When released, the trigger 16 is returned to an initial position by a return spring 22. This, in turn, returns the shuttle 20 to its initial position. Thus, actuation of the trigger 16 displaces the shuttle 20 both distally and proximally. While a specific linkage and trigger mechanism are depicted in the figure, different triggers and transmission linkages are envisioned. For example, a transmission linkage may incorporate gears, multi-bar linkages, or any other appropriate transmission mechanisms. In other embodiments, the transmission linkage is constructed to provide a mechanical advantage for displacing shuttle 20.

In the depicted embodiment, a system for deploying a surgical fastener from the surgical instrument includes a driveshaft 24 which extends distally from the handle 12 through an internal lumen of the elongated shaft 14. In another embodiment, the driveshaft may be completely disposed within the handle. The driveshaft 24 is coupled to the shuttle 20 such that proximal and distal movement of the shuttle shifts the driveshaft between a first proximal position and a second distal position. The driveshaft 24 is configured and arranged to apply a force to a distally located fastener, either directly or indirectly, to deploy the fastener from the surgical instrument.

As shown in FIGS. 1-4, the depicted power assist device includes an energy storage member 28, a striker 30, and an impact surface 32. The power assist device may also include an energy storage member housing 26 and a locking mechanism 34. The power assist device may be disposed within the handle 12. As illustrated in the figures, an energy storage member housing 26 may be coaxially aligned with the driveshaft 24 that extends distally from the handle. Depending upon the particular embodiment, the energy storage member housing 26 may be coupled directly to the driveshaft 24 such that axial displacement of the driveshaft causes a corresponding displacement of the energy storage member housing. In alternative embodiments, the energy storage member housing 26 may be free to move either rotationally and/or axially relative to the driveshaft 24 as the current disclosure is not limited in this fashion. As depicted in the figures, in some instances the energy storage member housing 26 directly contacts and/or is coupled to the shuttle 20. Depending on the particular embodiment, this contact and/or coupling may permit rotation of the energy storage member housing 26 relative to the shuttle 20.

As best illustrated in FIGS. 2 and 3, the energy storage member 28 may be coaxially disposed on the driveshaft 24 and partially disposed within an interior volume 52 of the energy storage member housing 26. A portion of the energy storage member 28 extends distally outwards from the interior volume 52. As shown in FIG. 4, the interior volume 52 includes a counter bore 52a and a through hole 52b. A shelf 54 is located between the counter bore 52a and the through hole 52b. When the energy storage member 28 is located within the interior volume 52, a proximal end of the energy storage member rests on a shelf 54. Thus, displacing the energy storage member housing 26 in a distal direction results in the energy storage member 28 being displaced in the distal direction. In instances where a distal end of the energy storage member 28 is locked in place, this distal displacement results in the energy storage member 28 being compressed.

While a through hole and a counter bore have been depicted for positioning and retaining the energy storage member, other arrangements for preventing proximal movement of the energy storage member are also envisioned including, but not limited to: one or more protrusions located within a through hole; fasteners; interlocking geometries; adhesives; interference fits; and other appropriate methods. Similarly, while the current embodiment depicts the energy storage member 28 as being at least partially disposed within the energy storage member housing 26, embodiments in which the energy storage member 28 is not disposed within another component of the power assist device are also possible. For example, the energy storage member may be coupled to the exterior of a component and in some instances the energy storage member may be in direct contact with the shuttle 20 without an intermediary component located between them.

While a coil spring has been illustrated for the energy storage member 28, the energy storage member is not so limited. For example, the energy storage member may include, but is not limited to, a magazine spring, gas spring, and any other appropriate structure or device capable of storing and releasing compression energy during actuation of the driveshaft.

In the illustrated embodiment, the striker 30 is disposed coaxially with the driveshaft 24. Striker 30 includes a striker head 30a, a shaft 30b, and a through hole 46 that extends through both the striker head 30a and shaft 30b. Through hole 46 is sized to allow the driveshaft 24 to freely move relative to the striker 30. In addition to being coaxially mounted with the driveshaft 24, the energy storage member 28 is mounted on the shaft 30b such that both the energy storage member 28 and shaft 30b are disposed within an interior volume 52 of the energy storage member housing 26. While the energy storage member 28 is restrained by the shelf 54, the shaft 30b passes through the counter bore 52a and through hole 52b. Shaft 30b and through hole 52b are sized such that the shaft 30b may freely slide within the through hole 52b. Since shaft 30b may freely slide within the through hole 52b, the shaft 30b is able to move relative to the energy storage member housing 26. Energy storage member 28 is located between the striker 30 and energy storage member housing 26. Consequently, movement of the driveshaft 24 and the energy storage member housing 26 in a distal direction relative to the striker 30, while the striker 30 is locked in place, compresses the energy storage member 28 between the striker head 30a and shelf 54 of the energy storage member housing 26.

Referring to FIGS. 1 and 2, locking mechanism 34 prevents release of the compressed energy storage member 28. As illustrated in the figures, locking mechanism 34 is a latch constructed and adapted to interact with a catch 30c located on the striker. Locking mechanism 34 is biased towards the locked position by a biasing member 36. Biasing member 36 may be any appropriate structure including but not limited to: a coil spring; a linear spring; a torsion spring; an elastic member incorporated into either the handle, latch, or other component that biases the latch towards the closed position; or any other appropriate structure. Locking mechanism 34 is moved to the unlocked position through the use of a camming surface 38 located on the energy storage member housing 26 and a camming surface 40 located on the locking mechanism 34. As described in more detail below, as the energy storage member housing 26 is displaced in the distal direction, the camming surface 36 comes into contact with the camming surface 40 and displaces the latching mechanism outwards which releases the striker 30. While the use of complimentary camming surfaces is depicted in the figures, other configurations are also possible. For example, the locking mechanism 34 may include: a rack and pinion arrangement to displace the locking mechanism; linkages to displace the locking mechanism; ratchet and pawl arrangements to selectively lock the striker 30 in place; or any other appropriate construction for selectively locking the striker 30 in place or controlling the operation of the locking mechanism 34.

When the locking mechanism 34 is moved to the unlocked position, the striker 30, and in turn the energy storage member 28, is released, allowing the energy storage member 28 to accelerate the striker 30 in the distal direction towards the impact surface 32. In the depicted embodiment, the impact surface 32 is a collar coupled to the driveshaft 24. Upon being struck, the driveshaft 24 accelerates in a distal direction to deploy a fastener.

While the various components of the power assist device such as the energy storage member housing, energy storage member, and striker have been depicted as being axially aligned with the driveshaft, embodiments in which the components of the power assist device are not axially aligned with the driveshaft are also envisioned. For example, the power assist device might be located adjacent to the driveshaft. In addition, while the power assist device may be disposed within the handle as depicted in the figures, the power assist device may also be located within a separate housing connected to handle 12.

In some embodiments, and as depicted in the figures, features such as the catch 30c and camming surface 38 are oriented in a preselected orientation to enable interaction with corresponding components such as the locking mechanism 34 and camming surface 40. In such an embodiment, it is desirable to maintain the preselected orientation of these components to enable the desired functionality of the power assist device. Therefore, in some embodiments, alignment features are provided on one or more components of the power assist device. As shown in FIG. 2, the energy storage member housing 26 may include a housing alignment feature 48 and striker 30 may include a striker alignment feature 50. The depicted alignment features are protrusions that interact with slots, grooves, walls, or other appropriate features present on the handle interior (not depicted) to maintain the orientation of the energy storage member housing 26 and striker 30 during actuation of the device. While the current embodiment employs alignment features, other embodiments are also possible. For example, a camming and/or catch surface could be located around the entire perimeter of a component such that the component would work in any orientation.

With regards to the above embodiment, the impact surface 32 and the striking surface 44 may be made from any appropriate material. For example, appropriate materials for the impact surface and striking surface may include, but are not limited to, metals such as steel, stainless steel, aluminum, and titanium as well as rigid plastics and composite materials. In some embodiments, these components are made from the same material, though other embodiments in which the impact surface and striking surface are made from different materials are also possible. In addition, while specific geometries have been shown for the impact surface and striking surface, these components are not limited to any specific shape, size, or arrangement. Instead, the current disclosure should be viewed generally as disclosing impacting any appropriate surface associated with the driveshaft with an appropriately constructed and arranged mass to transfer momentum thereto to deploy a fastener.

To improve the energy transfer from the striker to the driveshaft, the impact surface 32 and striking surface 44 may be constructed and arranged, and/or made from a material, to provide a high coefficient of restitution. For example, the coefficient of restitution for the strike between the impact surface and striking surface may be greater than or equal to about 0.7, 0.75, 0.8, 0.85, 0.9, 0.95, or any other appropriate numerical coefficient. Correspondingly, the coefficient of restitution may be less than or equal to about 1, 0.95, 0.9, 0.85, 0.8, 0.75, or any other appropriate numerical coefficient. Thus, combinations of the above ranges are contemplated (e.g., a coefficient of restitution for the strike greater than or equal to about 0.8 and less than or equal to about 1). Other combinations are also possible. Further, embodiments in which the coefficient of restitution for the strike between the impact surface and striking surface is less than those noted above are also envisioned.

Figure 5A:
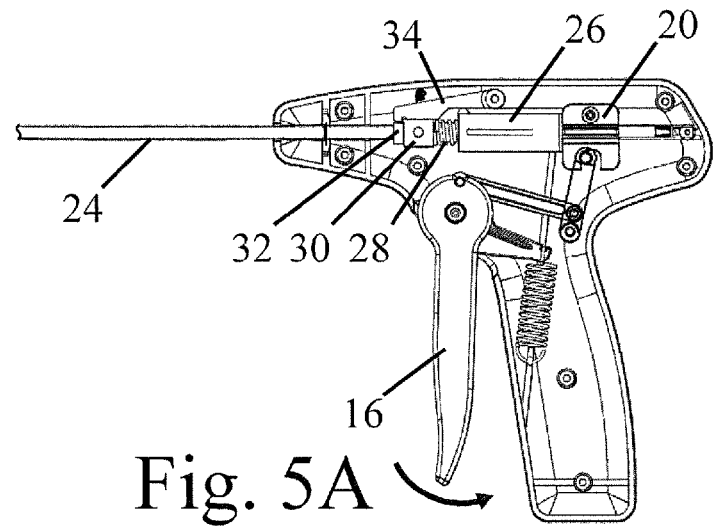
FIG. 5A is a cross-sectional view of a surgical instrument incorporating a power assist device during actuation and prior to energy storage in the power assist device.
Figure 5B:
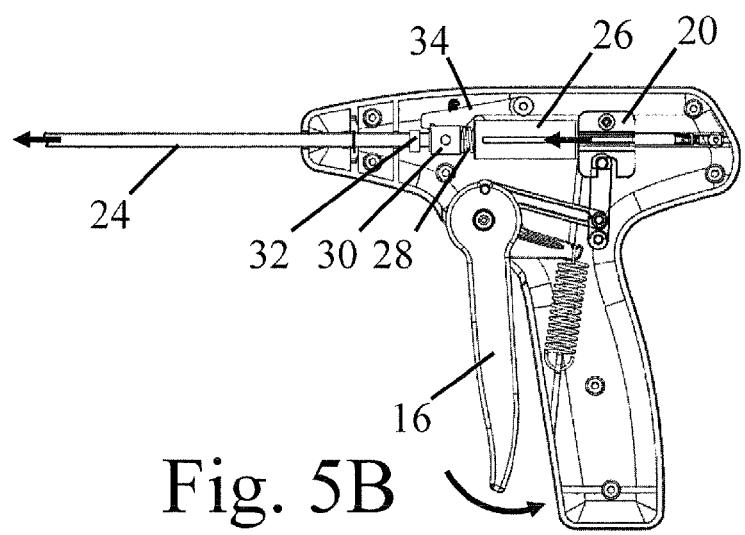
FIG. 5B is a cross-sectional view of a surgical instrument incorporating a power assist device during actuation with energy stored in the energy storage member.
Figure 5C:
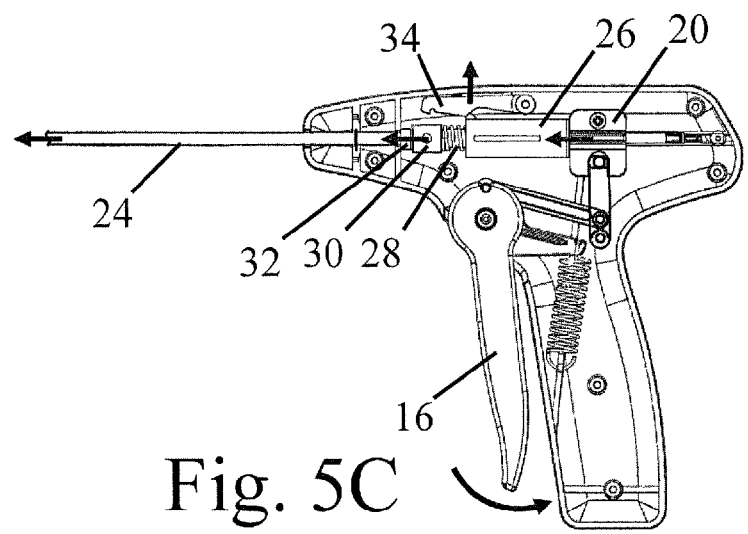
FIG. 5C is a cross-sectional view of a surgical instrument incorporating a power assist device during actuation after release of the striker.

Turning now to FIGS. 5A-5C, operation of the embodiment illustrated in FIGS. 1-4 is described in more detailed.

In FIG. 5A, actuation of trigger 16 begins. Trigger 16 has a predetermined amount of play prior to the engaging shuttle 20 to actuate the driveshaft 24. In other embodiments, the amount of play in the trigger actuation may be reduced, or the trigger may not have any play in the actuation as the current disclosure is not limited in this fashion.

Further actuation of the trigger 12, shown in FIG. 5B, engages and moves the shuttle 20 in a distal direction. As the shuttle 20 is moved in the distal direction, the driveshaft 24, impact surface 32, and energy storage member housing 20 are correspondingly moved in the distal direction. Since the striker 30 is retained in the locked position by the locking mechanism 34, the energy storage member 28 is compressed between the energy storage member housing 26 and the striker 30. In addition to compressing the energy storage member 28, the drive shaft 24 may partially deploy a fastener from the end of the elongated shaft 14 prior to release of the striker 30 as it is moved in the distal direction. This partial deployment of the fastener may act as a piloting stage of the fastener deployment.

Referencing FIG. 5C, upon further actuation of the trigger 12, the shuttle 20 continues to displace the driveshaft 24 and the energy storage member housing 26 in a distal direction, storing additional energy in the energy storage member 28. At a preselected position, the camming surface 38 on the energy storage member housing 26 displaces the locking mechanism 34 outwards to unlock the striker 30. Once unlocked, the striker 30 is accelerated in a distal direction by the energy storage member 28, ultimately striking the impact surface 32 to transfer momentum to the driveshaft 24. The resulting impulse to the driveshaft 24 accelerates the movement of the driveshaft 24 in the distal direction to fully deploy the associated fastener. Prior to the striker 30 striking the impact surface 32, the drive shaft may move at a first speed in the distal direction. Subsequent to the striker 30 striking the impact surface 32, the drive shaft may move at a second speed in the distal direction greater than the first. Trigger 16 is now released, and the driveshaft 24, striker 30, energy storage member 28, energy storage member housing 26, and shuttle 20 move in the proximal direction and return to their initial positions as depicted in FIG. 5A to reset the device for deploying the next fastener.

Figure 6:
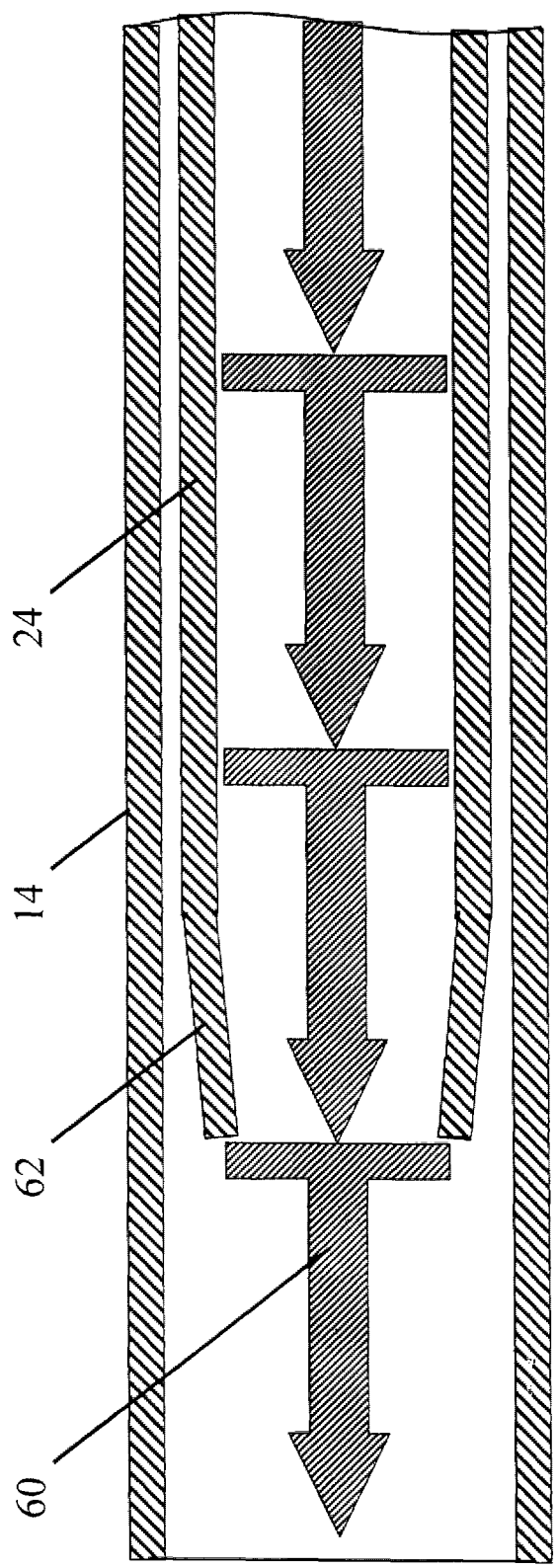
FIG. 6 is a cross-sectional view of a distal end of the elongated shaft including the driveshaft and surgical fasteners.

FIG. 6 is a cross-sectional view of one possible, embodiment of a distal end of the elongated shaft 14. As depicted in the figure, one or more fasteners 60 may be disposed within the elongated shaft of the surgical instrument. As noted above, the driveshaft 24 of the system for deploying a surgical fastener from the surgical instrument reciprocates in the distal and proximal directions during actuation of the surgical instrument. As the driveshaft 24 is displaced in the distal direction, one or more tabs 62 located on the distal end of the driveshaft 24 engage a portion of the distal most fastener 60 to drive the fastener out of the distal end of the elongated shaft. In some embodiments, the remaining fasteners located proximally from the distal most fastener may be moved in a distal direction at the same time as, or subsequent to, the deployment of the distal most fastener to position the next distal most fastener for deployment. After deploying the fastener, the driveshaft 24 may be moved in the proximal direction to draw the tabs 62 over the next fastener to reset the surgical instrument for the next fastener deployment.

While a specific arrangement for the deployment of a fastener from the distal end of the surgical instrument has been described above and shown in FIG. 6, it should be understood that other arrangements are also possible. For example, in one embodiment, the driveshaft might be constructed as a sled to guide and drive the fasteners simultaneously. In another embodiment, the driveshaft might be located on a separate axis than the fasteners such that the distal most fastener is moved into alignment with the driveshaft prior to deployment. In yet another embodiment, the driveshaft might be operatively associated with the fastener through a separate component, or assembly. More specifically, in such an embodiment, distal movement of the driveshaft might provide energy to, or displace the separate component, or assembly, to indirectly deploy the fastener. The above embodiments are only meant to be illustrative, and the current disclosure should not be limited to only those embodiments disclosed herein in. Instead, any appropriate driveshaft and the one or more fasteners may be used. Further, the driveshaft and the one or more fasteners may be arranged and configured in any appropriate fashion such that distal movement of the driveshaft deploys a fastener.

In the above embodiments, a device with a unitary handle and elongated shaft 14 that is stationary relative to the handle is described. However, in some embodiments, it is desirable to provide an elongated shaft 14 that is capable of being rotated relative to the handle to facilitate positioning of a fastener. In such an embodiment, either the shaft, or a portion of the handle, may be rotatable relative to the portion of the handle including the grip. One such embodiment is depicted in FIGS. 7-10. In the depicted embodiment, the device 10 includes a first handle portion 100 that is rotatable relative to a second handle portion 102. The first and second handle portions 100 and 102 may be constructed and arranged in any appropriate fashion to be rotatable relative to one another. The handle 12 also includes a rotational housing 104 for housing the power assist device. In some embodiments, the rotational housing 104 includes a coupling 106 that maintains the orientation of the rotational housing relative to the first handle portion. However, embodiments in which the rotational housing 104 is free to rotate within the first portion 100 are also envisioned.

Figure 7:
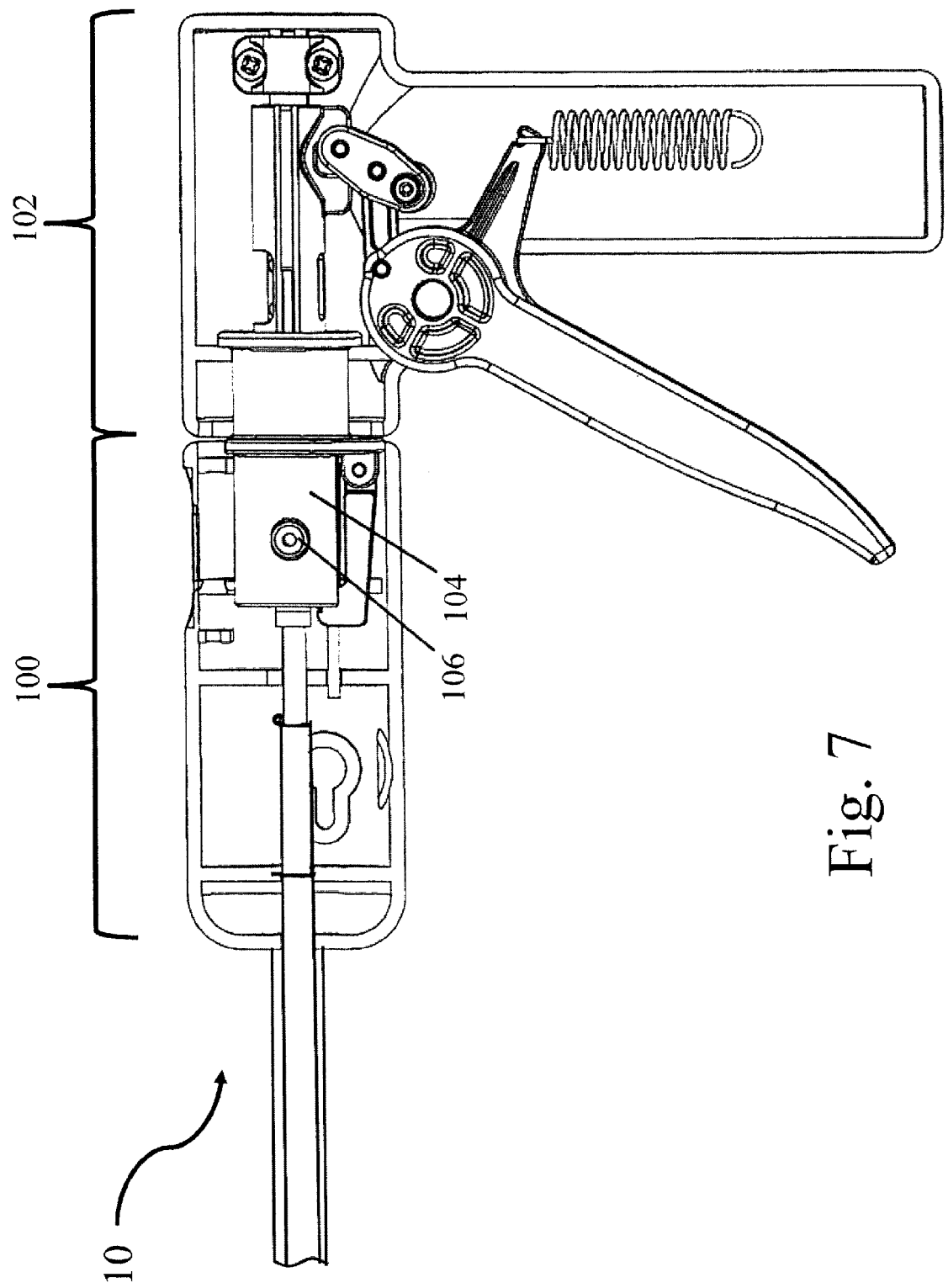
FIG. 7 is a cross-sectional view of a surgical instrument incorporating a power assist device and a rotational coupling.
Figure 8:
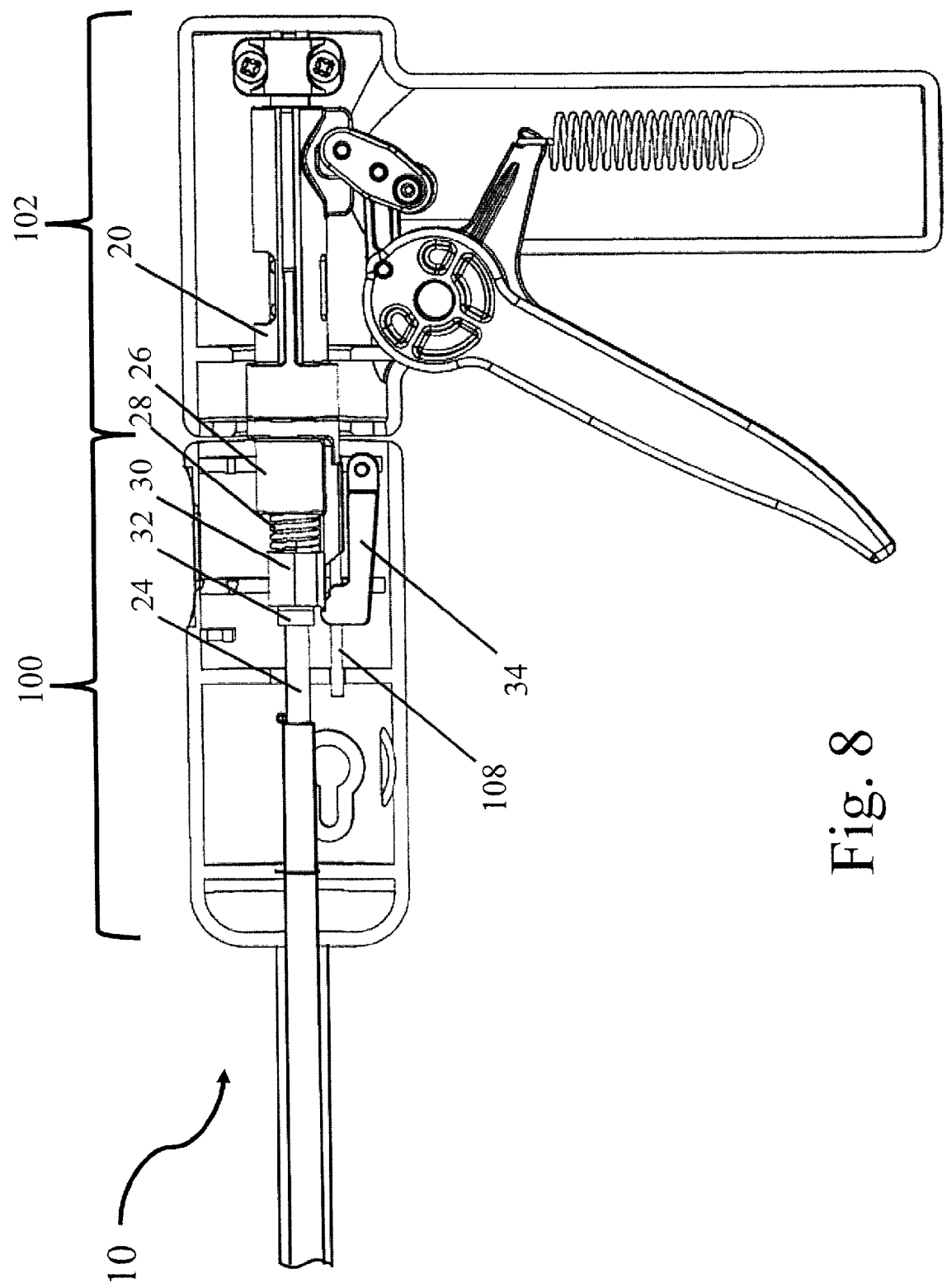
FIG. 8 is a cross-sectional view of a surgical instrument incorporating a power assist device and a rotational coupling with the rotational housing removed to illustrate the power assist device.

FIG. 8 depicts the device of FIG. 7 with the rotational housing removed to show the power assist device and its individual components. Similar to the arrangements described above, the power assist device may include an energy storage member housing 26, energy storage member 28, striker 30, impact surface 32, and locking mechanism 34. However, in the current embodiment, these components are incorporated within a rotational housing 104 such that when the first handle portion 100 is rotated the orientation of these components with respect to the second handle portion 102 changes. In addition, in some embodiments in which the drive shaft does not rotate, the orientation of these components may also change relative to the driveshaft as well. To facilitate rotation of the power assist device relative to the second handle portion 102, the shuttle 20 is either rotatably coupled to the energy storage member housing 26, or the shuttle 20 may simply contact energy storage member housing 26 without being physically connected thereto. By permitting rotation between the energy storage member housing 26 and the shuttle 20, the shuttle 20 is still able to distally displace the energy storage member housing while permitting rotation as well.

Figure 9:
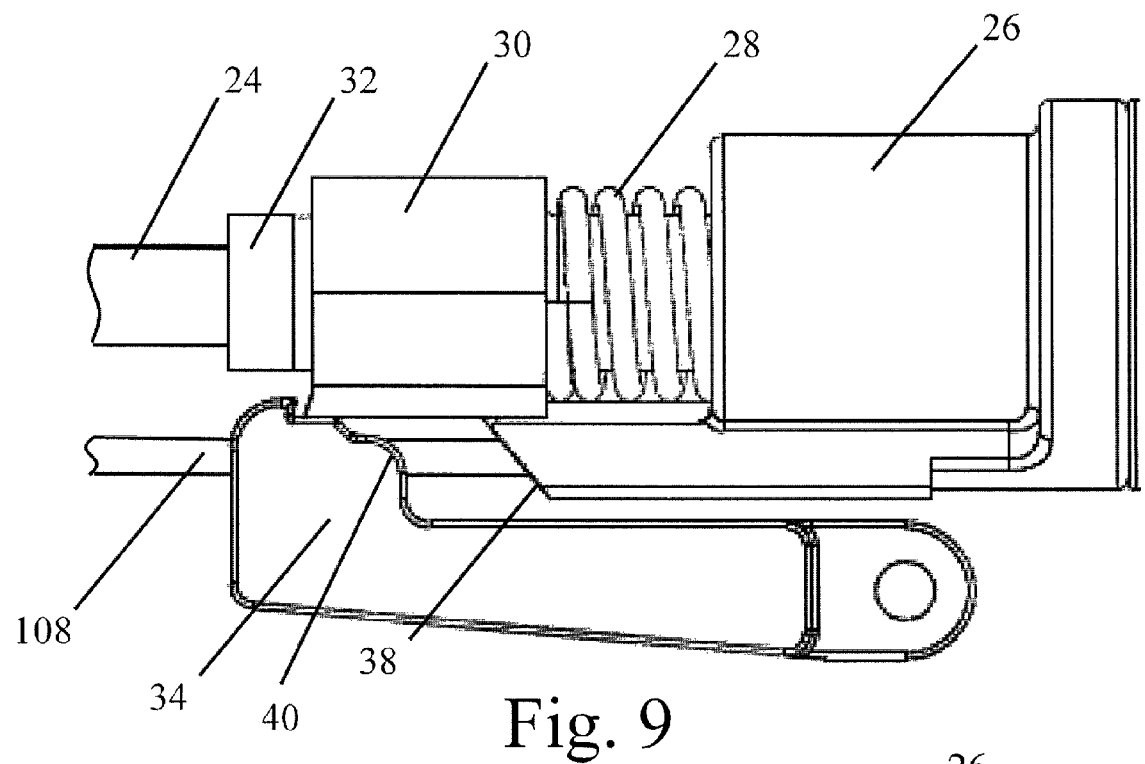
FIG. 9 is a cross-sectional view of the power assist device of FIGS. 7 and 8.
Figure 10:
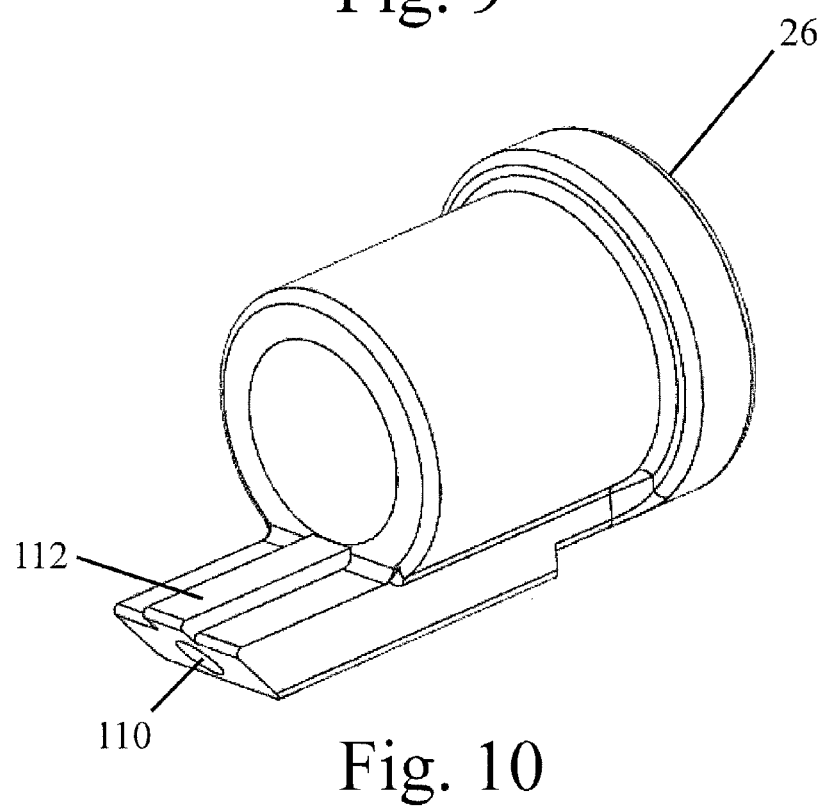
FIG. 10 is a perspective view of the energy storage member housing of the power assist device of FIGS. 7 and 8.

To maintain the relative orientation of the various components of the power assist device, an alignment feature such as an alignment shaft 108 may be provided. The alignment shaft 108 may be connected directly to the first handle portion 100, or, alternatively, the alignment shaft 108 may be connected to the rotational housing 104 to maintain the orientation of the components. As shown in FIGS. 9 and 10, the alignment shaft 108 controls the orientation of the various components of the power assist device by controlling the orientation of the energy storage member housing 26. In the illustrated embodiment, the energy storage member housing 26 includes an alignment hole 110 that axially extends through the energy storage member housing 26. In some embodiments, the alignment hole 110 only extends through a portion of the energy storage member housing 26. The alignment hole 110 is sized to permit the energy storage member housing 26 to be freely displaced along the alignment shaft 108. The energy storage member housing 26 also includes an alignment rail 112, or other appropriate feature, that interacts with a corresponding groove located on the striker 30, not depicted. Therefore, due to the energy storage member housing 26 being maintained in the appropriate position via the alignment shaft 108, the striker 30 is maintained in the appropriate alignment with locking mechanism 34 by the alignment rail 112.

In some embodiments, it is desirable to permit a fastener to be deployed even in the event of the power assist device being nonfunctional. This may be of benefit since the device would still be capable of use even without the additional power provided by the power assist device. In order to permit a fastener to be deployed in the event of the power assist device being disabled, the various dimensions of the energy storage member housing, energy storage member, the striker, and the location of the impact surface relative to these components would be selected such that the energy storage member could be compressed through a full actuation of the driveshaft to deploy a fastener. Thus, even if the striker 30 were not released to impart an impulse to the driveshaft 24, the driveshaft would still be fully actuatable. This is in contrast to other embodiments in which the dimensions of various components would either fully compress the energy storage member 28, or contact a proximal surface of the striker 30 with the energy storage member housing 26, prior to full actuation of the driveshaft. In such an instance, the driveshaft would be precluded from undergoing a full actuation and fully deploying a fastener.

While the above embodiments have described a power assist device that is coaxially located with the driveshaft, other embodiments are also envisioned. For example, in one embodiment, one or more components of a power assist device might be located adjacent to, or even possibly removed from, the driveshaft. Without wishing to be bound by theory, such embodiment may be beneficial in that it would help to prevent acceleration of the driveshaft in a proximal direction due to the acceleration of the striker. In one such embodiment, the energy storage member housing, energy storage member, and striker may be located adjacent and substantially parallel to the driveshaft. In such an embodiment, the energy storage member housing would be displaced by a power transmission coupled to the trigger or even possibly the driveshaft to store energy in the energy storage member. Similar to the above embodiments, after a preselected amount of displacement of the driveshaft, the striker would be released and subsequently strike an impact surface coupled to the driveshaft to transfer momentum to the driveshaft and deploy a fastener.

It should be understood that the current disclosure is not limited to any particular displacement direction of the driveshaft. For example, in some embodiments, instead of displacing the driveshaft in an axial direction, the driveshaft may be displaced in a rotary direction. Consequently, the driveshaft may be displaced axially, rotatably, or in any other appropriate fashion. Further, the striker and impact surface may be constructed and arranged in any appropriate manner to facilitate displacement of the driveshaft in the desired direction.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

What is claimed is:

1. A surgical instrument comprising:
a handle;
an elongated shaft extending from the handle;
a surgical fastener deployment system including a driveshaft, wherein the driveshaft is actuatable between at least a first proximal position and a second distal position;
a striker movable relative to the driveshaft;
an impact surface associated with the driveshaft, wherein the striker strikes the impact surface to displace the driveshaft to the second distal position and deploy the surgical fastener; and
an energy storage member to accelerate the striker in a distal direction, the energy storage member being operatively associated with the driveshaft, wherein actuation of the driveshaft from the first proximal position towards the second distal position stores energy in the energy storage member.

2. The surgical instrument of claim 1, wherein the impact surface is directly coupled to the driveshaft.

3. The surgical instrument of claim 1, wherein the driveshaft directly deploys a surgical fastener from the elongated shaft.

4. The surgical instrument of claim 1, further comprising a locking mechanism that selectively locks the striker in place.

5. The surgical instrument of claim 4, wherein the locking mechanism releases the striker to strike the impact surface when the driveshaft is located at a preselected position between the first proximal position and the second distal position.

6. The surgical instrument of claim 5, wherein the driveshaft is moving in a distal direction when the locking mechanism releases the striker.

7. The surgical instrument of claim 5, wherein the locking mechanism includes a first camming surface that is displaced as the driveshaft is actuated from the first proximal position towards the second distal position to release the striker.

8. The surgical instrument of claim 7, wherein a second camming surface associated with the driveshaft displaces the first camming surface as the driveshaft is actuated from the first proximal position towards the second distal position.

9. The surgical instrument of claim 1, wherein the driveshaft, striker, and energy storage member are coaxially located.

10. The surgical instrument of claim 1 further comprising an energy storage member housing coupled to the driveshaft, wherein the energy storage member is coupled with the energy storage member housing, and wherein displacement of the driveshaft and energy storage member housing relative to the striker stores the energy in the energy storage member.

11. The surgical instrument of claim 10 wherein the energy storage member housing is rotatable relative to at least a portion of a handle of the surgical instrument.

12. The surgical instrument of claim 10, wherein the energy storage member housing includes an alignment feature to align the energy storage member housing and the driveshaft.

13. The surgical instrument of claim 1, wherein the striker is rotatable relative to at least a portion of a handle of the surgical instrument.

14. The surgical instrument of claim 1, wherein the impact surface is a collar disposed on the driveshaft.

15. The surgical instrument of claim 1, wherein the drive shaft is accelerated from a first speed to a second speed when the impact surface is struck by the striker.

16. A surgical instrument comprising:
a handle;
an elongated shaft extending from the handle;
a surgical fastener deployment system including a driveshaft and an impact surface associated with the driveshaft that is moveable in a distal direction relative to the handle, wherein the driveshaft is actuatable between at least a first proximal position relative to the handle and a second distal position relative to the handle; and a striker, wherein actuation of the surgical fastener deployment system displaces the driveshaft from the first proximal position relative to the handle towards the second distal position relative to the handle and the striker strikes the impact surface as the impact surface and driveshaft move in the distal direction relative to the handle to displace the driveshaft to the second distal position relative to the handle and deploy the surgical fastener.

17. The surgical instrument of claim 16, wherein the striker is rotatable relative to at least a portion of a handle of the surgical instrument.

18. The surgical instrument of claim 16, further comprising a locking mechanism that selectively locks the striker in place.

19. The surgical instrument of claim 18, wherein the locking mechanism releases the striker to strike the impact surface when the driveshaft is located at a preselected position between the first proximal position and the second distal position.

20. The surgical instrument of claim 16, wherein the drive shaft is accelerated from a first speed to a second speed when the impact surface is struck by the striker.

21. The surgical instrument of claim 16,
wherein the driveshaft and striker are coaxially located and the striker extends at least partially along a length of the driveshaft.

22. The surgical instrument of claim 21, further comprising an energy storage member to accelerate the striker in the distal direction relative to the handle.

23. The surgical instrument of claim 22, wherein the driveshaft, striker, and energy storage member are coaxially located.

24. A surgical instrument comprising:
a handle;
an elongated shaft extending from the handle;
a surgical fastener deployment system including a driveshaft, wherein the driveshaft is actuatable between at least a first proximal position and a second distal position;
a striker movable relative to the driveshaft;
an impact surface associated with the driveshaft, wherein the striker strikes the impact surface to displace the driveshaft to the second distal position and deploy the surgical fastener;
a locking mechanism that selectively locks the striker in place, wherein the locking mechanism includes a first camming surface that is displaced as the driveshaft is actuated from the first proximal position towards the second distal position to release the striker; and
a second camming surface associated with the driveshaft that displaces the first camming surface as the driveshaft is actuated from the first proximal position towards the second distal position.

25. The surgical instrument of claim 24, wherein the striker is rotatable relative to at least a portion of a handle of the surgical instrument.

26. The surgical instrument of claim 24, wherein the drive shaft is accelerated from a first speed to a second speed when the impact surface is struck by the striker.

* * * * *